US006998126B2

(12) United States Patent
Davelaar

(10) Patent No.: US 6,998,126 B2
(45) Date of Patent: Feb. 14, 2006

(54) **SELECTION OF POULTRY *EIMERIA* STRAINS THROUGH EXTRA-INTESTINAL SPOROZOITES**

(75) Inventor: Frans Gerrit Davelaar, Putten (NL)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/371,914

(22) Filed: Feb. 21, 2003

(65) Prior Publication Data

US 2003/0170277 A1 Sep. 11, 2003

Related U.S. Application Data

(60) Provisional application No. 60/360,088, filed on Feb. 26, 2002.

(51) Int. Cl.
*A61K 39/012* (2006.01)
*C12N 1/36* (2006.01)

(52) U.S. Cl. ............................ 424/267.1; 424/265.1; 424/273.1; 424/423; 424/269.1; 424/184.1

(58) Field of Classification Search ............. 424/184.1, 424/93.1, 271.1, 151.1, 269.1, 265, 267, 424/265.1, 451, 456, 457, 267.1, 185.1, 191.1, 424/69.1, 69.3, 423, 85.1, 9.2, 273.1, 276.1, 424/193.1; 435/7.2, 243, 693, 258.1, 252.3, 435/245, 258, 947, 7.32; 514/45, 266.22, 514/23, 55, 24, 8; 536/24.32; 530/350
See application file for complete search history.

(56) References Cited

U.S. PATENT DOCUMENTS

| 4,808,404 | A | * | 2/1989 | Bhogal ..................... 424/271.1 |
| 4,874,705 | A | | 10/1989 | Andrews et al. |
| 5,028,694 | A | | 7/1991 | Mewman, Jr. et al. |
| 5,055,292 | A | * | 10/1991 | McDonald et al. ....... 424/271.1 |
| 5,068,104 | A | * | 11/1991 | Bhogal et al. ............ 424/193.1 |
| 5,141,925 | A | * | 8/1992 | Alroy et al. .................. 514/23 |
| 5,187,080 | A | | 2/1993 | Andrews et al. |
| 5,885,568 | A | | 3/1999 | Tomley et al. |
| 5,932,225 | A | * | 8/1999 | Wallach et al. .......... 424/267.1 |
| 6,001,363 | A | | 12/1999 | Tomley et al. |
| 6,019,985 | A | | 2/2000 | Brown et al. |
| 6,100,241 | A | | 8/2000 | Kok et al. |
| 2003/0013822 | A1 | * | 1/2003 | Chisholm et al. ............. 526/78 |
| 2004/0120973 | A1 | * | 6/2004 | McDougald et al. ..... 424/265.1 |

FOREIGN PATENT DOCUMENTS

| EP | 0256 878 B1 | | 8/1987 |
| JP | 57-159720 | * | 10/1982 |
| JP | 402304031 A | * | 12/1990 |
| WO | WO 94/16725 | | 8/1994 |

OTHER PUBLICATIONS

Goldova, M. et al. 2000. Life cycle of *Eimeria procera* in experimentally infected grey partridges (*Perdix perdix*), Vet. Parasit. 90: 255-263.*
Rose, ME et al, Parasitology, 1991, Jun. vol. 102(pt 3), pp. 317-324, *Eimeria tenella*, localization of the sporszoites in the caecum of the domestic fowel.*
Kogut, MH et al, Z. Parasitenkd, 1984, vol. 70, pp. 287-295, Extraintestinal sporozoites of chicken *Eimeria* in chickens and turkeys.*
Augustine, PC et al, Avian Diseases, vol. 39, pp. 709-717, 1995, Eimeria tenella and E.acervulina: Differences in ability to elicit cross-species protection as compared with the Turkey Coccidium E.adenoeides.*
Long, PL et al, A guide to laboratory techniques used in teh study and diagnosis of avian coccidiosis, Folia Veterinaria Latina, 1976, Jul.-Sep. vol. 6(3), pp. 201-217.*
Ball, SJ et al, J. Parasit., vol. 76(3), pp. 424-425, 1990, Transfer of Extraintestinal stages of Eimeria vermiformis in the mouse.*
Al-Attar, MA et al, J. Parasitol., 1987, Jun., vol. 73(3), pp. 494-501, Transport of Eimeria necatrix sporozoites in the chicken: effects of irritants injected intraperritoneally.*
Van Doornick, WM et al, Transport of sporozoites of Eimeria necatrix in macrophages. J. parasitology, Feb. 1957, vol. 43(1), pp. 40-44.*
Fernando, MA et al, J. parasitology, vol. 73(3), pp. 561-567, 1987, Eimeria spp. of domestic fowl: The migration of sporozoites intra and extra enterically.*
Kogut et al (1984), reference of record.*
Williams, R.B., "Anticoccidial Vaccines for Broiler Chickens: Pathways to Success," Avian Pathology, 2002, pp. 317-353, vol. 31.
Jeffers, T.K., "Attenuation of Coccidia—A Review," presented at Georgia Coccidiosis Conference, Lake Lanier, GA, Nov. 17-21, 1985, pp. 482-501.
Williams, R.B. et al., "The efficacy and economic benefits of Paracox®, a live attenuated anticoccidial vaccine, in commercial trials with standard broiler chickens in the United Kingdom," International Journal for Parasitology, 1999, pp. 341-355, vol. 29.

(Continued)

*Primary Examiner*—Lynette R. F. Smith
*Assistant Examiner*—Ginny Allen Portner
(74) *Attorney, Agent, or Firm*—John F. Levis

(57) ABSTRACT

A method for obtaining an immunogenic strain useful for producing a vaccine against Coccidiosis comprises the cycle of infecting at least one first group of specific pathogen-free donor birds with oocysts from an *Eimeria* species. Blood is then collected from these donor birds, and is then used to infect a second group of specific pathogen-free birds. Oocysts are collected from the second group of birds. These oocysts are then multiplicated to complete the cycle. The cycle is then repeated using the multiplicated oocysts. After a total of about three cycles, a final antigen may be harvested and utilized as a source to generate oocysts for a vaccine.

15 Claims, No Drawings

OTHER PUBLICATIONS

Shirley, M.W. et al., "Eimeria Brunetti: Selection and Characteristics of a Precocious (and attenuated) Line," Avian Pathology, 1986, pp. 705-717, vol. 15.

Shirley, Martin W., et al., "Control of Coccidiosis in chickens: Immunization with Live Vaccines," CRC Press, Inc., Boca Raton, Florida, USA, pp. 322-329.

Supplementary European Search Report for EP 03 71 3628.

McDonald et al., A preliminary study of the nature of infection and immunity in chickens given an attenuated line of *Eimeria acervulina, Parasitology* (1982), 84, 21-30.

McDonald and Ballingall, Further investigation of he pathogenicity, immunogenicity and stability of precocious *Eimeria acervulina, Parasitology* (1983), 86, 361-369.

Williams and Catchpole, A new protocol for a challenge test to assess the efficacy of live anticoccidial vaccines for chickens, *Vaccine* 18 (2000) 1178-1185.

Lillehoj, Review on Vaccine Development Against Enteric Parasites Eimeria and Cryptosporidium, *Jpn. Poult. Sci,* 37: 117-141, (2000).

Shirley and Bedrnik, Live Attenuated Vaccines against Avian Coccidiosis: Success with Precocious and gg-adapted Lines of *Eimeria, Parasitology Today,* vol. 13, No. 12, 1997, 481-484.

Mc Dougald, et al., "Coccidiosis," *Diseases of Poultry* by Bruce Calnek, editior, 1991, pp. 780-797, Iowa State Univeristy Press, ISBN 0-8138-429-9.

* cited by examiner

SELECTION OF POULTRY *EIMERIA* STRAINS THROUGH EXTRA-INTESTINAL SPOROZOITES

This application claims priority from copending provisional application(s) Ser. No. 60/360,088 filed on Feb. 26, 2002.

FIELD OF THE INVENTION

The present invention relates to a poultry vaccine, and more particularly, to a novel vaccine against Coccidiosis. The invention also relates to newly developed strains of *Eimeria* species with strong immunogenic properties and low pathogenicity which are useful in producing oocysts for anti-coccidia vaccines. In addition, the invention is directed to novel methods of obtaining attenuated strains of *Eimeria* species which are useful in formulating vaccines against Coccidiosis.

BACKGROUND OF THE INVENTION

Cocciodiosis is an avian disease caused by infection with one or more of the many species of coccidia, which are intracellular protozoal parasites of the subphylum Apicomplexa and the genus *Eimeria*. Cocciodiosis is known to be caused by several different species of *Eimeria*, namely *Eimeria acervulina, E. maxima, E. tenella, E. necatrix, E. brunetti, E. mitis, E. praecox*, and possibly *E. mivati* and *E. hagani*. The species do differ in their pathogenic effect on birds, with the type of birds also playing a role. Thus, a broiler chicken will be subjected to a great deal of damage by a parasite such as *E. acervulina* because it infects large portions of the small intestine, where food digestion plays a major role.

During its life cycle, the *Eimeria* parasite passes through a number of stages. The life cycle begins when the chicken ingests the infectious stage, known as the sporulating oocyst, during ground feeding or by inhalation of dust. The wall of the sporulated oocyst is ruptured by the mechanical action in the gizzard and intestinal tract, resulting in the release of four sporocysts. The sporocysts pass into the duodenum where they are exposed to bile and digestive enzymes resulting in the release of an average of two sporozoites per sporocyst.

The sporozoites are mobile and search for suitable host epithelium cells in order to penetrate and reproduce in them. Following infection of an epithelium cell, the parasite enters the schizont phase of its life cycle, producing from 8 to 16 to greater than 200 merozoites per schizont. Once released from the schizont, the merozoites are free to infect further epithelium. After from two to five of these asexual reproduction cycles, the intracellular merozoites grow into sexual forms known as the female or macrogametocyte and the male or microgametocyte. Following fertilization of the macrogametocyte by the microgametes released from the microgametocyte, a zygote is formed which creates a cyst wall about itself. The newly formed oocyst is passed out of the infected chicken with the droppings.

With the correct environmental conditions of temperature and humidity and sufficient oxygen in the air, the oocyst will sporulate into the infectious stage, ready to infect a new host and thereby spread the disease. Thus, no intermediate host is required for transfer of the parasite from bird to bird.

The result of the *Eimeria* parasite infecting the digestive tract of a bird may be a reduction in weight gain, decreased feed conversion, cessation of egg production and, in some cases, death. The increase in intensive production of poultry has been accompanied by severe losses due to this parasite. It is estimated that losses in the United States and Europe exceed several hundred million dollars annually.

Several attempts have now been made to control Coccidiosis. Prior to the advent of chemotherapeutic agents, improved sanitation using disinfectants, together with mechanical removal of litter, were the main methods employed. In addition, the introduction of coccidiostatic agents in the feed or drinking water, along with good management practices, has resulted in some success at disease control. However, such agents have been found to suffer from a drop in effectiveness over the years, due partly to the development of drug resistant strains of coccidia. Furthermore, several chemotherapeutic agents have been found to leave residues in the meat of commercial birds, thereby often making it unsuitable for consumption.

Other attempts to control the disease have been made immunologically. These have included the development of live vaccines and the use of genetic engineering to formulate vaccines. Many of these efforts have focused on the use of *Eimeria* proteins as the active component of the vaccine. For example, Tomley et al. in U.S. Pat. Nos. 5,885,568 and 6,001,363 propose an Eimeria protein with immunogenic properties, as well as DNA sequences which encode these proteins. A similar approach is set forth in Kok et al., U.S. Pat. No. 6,100,241. A DNA molecule having a particular nucleic acid sequence is set forth in Andrews et al., U.S. Pat. No.s 4,874,705 and 5,187,080, while Mewman et al., U.S. Pat. No. 5,028,694, describes a purified antigenic protein which is capable of inducing an immune response in a chicken against *Eimeria necatrix* or *Eimeria tenella*. A vaccine against Coccidiosis is also described in Brown et al., U.S. Pat. No. 6,019,985.

What is now needed in the art is a new vaccine against Coccidiosis which is safe, effective, easy to administer and cost efficient. Also needed are new strains of *Eimeria* species which can be used in eliciting an immune response in poultry, so as to provide suitable oocysts for a vaccine. Further needed are new methods of attenuating strains of *Eimeria* so that they can be utilized for vaccine development. The art further necessitates the development of strains of Eimeria whose oocysts, when incorporated into a vaccine, are cross-protective against a wider sampling of *Eimeria* species.

SUMMARY OF THE INVENTION

It is therefore an object of the present invention to provide an isolated *Eimeria* strain which is useful in generating oocysts for a vaccine against Coccidiosis.

Also provided as part of the invention is a vaccine effective against Coccidiosis in poultry, which comprises at least about $10^4$ oocysts of attenuated *Eimeria* per dose, together with a pharmaceutically acceptable carrier.

Further provided is a method of inoculating poultry against Coccidiosis, which comprises administering to said poultry at least about $10^4$ oocysts from attenuated *Eimeria acervulina*.

The invention also provides a method for obtaining an immunogenic *Eimeria* strain which is useful for producing oocysts for a vaccine against the poultry disease Coccidiosis, which comprises the cycle of a) infecting at least one specific pathogen-free donor bird with oocysts from an *Eimeria* species; b) collecting blood from the donor bird; c) infecting at least one second specific pathogen-free bird with the blood from the donor bird; d) collecting oocysts from the second bird; and e) multiplicating the oocysts to substantially complete the cycle. The cycle is then repeated at least two more times (at least three total) using the multiplicated oocysts from sub-procedure e) of the immediately proceeding completed cycle.

In a further aspect of the invention there is a method of attenuating one or more strains of *Eimeria*, which comprises successively passaging the strain through at least three sets of specific pathogen-free poultry, wherein each of the passages comprises at least two successive sets of inoculations.

The invention also provides another method for attenuating *Eimeria acervulina*, which comprises the cycle of:
 a) inoculating at least one first group of specific pathogen-free donor birds with oocysts generated from virulent *E. acervulina*;
 b) collecting blood from this first group of donor birds via bleeding at about 3 to about 6 hours post-inoculation;
 c) inoculating at least one second group of specific pathogen-free donor birds with the derived blood;
 d) collecting oocysts from the second group of birds; and
 e) multiplicating the oocysts to thereby substantially complete the cycle; and
then repeating the cycle using the multiplicated oocysts from sub-procedure e), wherein about three cycles are completed.

In addition to the foregoing, the invention also provides oocysts derived from *Eimeria* species, in particular *E. acervulina*, in which the *E. acervulina* has been attenuated by about three cycles of passaging through specific pathogen-free poultry.

In a further embodiment of the invention, there is provided a strain of *Eimeria* having the immunogenic characteristics of the strain *E. acervulina* deposited with the European Collection of Cell Cultures under accession number 02010911.

Also provided is a vaccine, said vaccine having the immunogenic response properties of a vaccine against Coccidiosis which contains an immunogenizing amount of oocysts obtained from the strain of *E. acervulina* deposited with the European Collection of Cell Cultures under accession number 02010911.

The foregoing and other features and advantages of the invention will become more apparent from the detailed description of the preferred embodiments of the invention given below.

DETAILED DESCRIPTION OF THE PREFERRED EMBODIMENTS

The invention in all its embodiments hereinafter described is contemplated for use with all poultry. As that term is used herein, "poultry" shall refer to domesticated birds that serve as a source of eggs or meat and shall include, without limitation, such commercially important species as chickens, turkeys, ducks, geese, guinea fowl, pheasants, pigeons, peafowl, bantam fowl and the like.

The terms "immunogenic strain" and "antigenic strain" shall also be used interchangeably, and shall refer to one or more whole organism(s) or fragment(s) thereof, including protein(s), polypeptide(s), or sequence(s) of amino acids, which is/are useful in inducing or eliciting an immune response in an animal such as poultry. Those skilled in the art will recognize that an immune response is generally recognized by the production of antibodies and/or cellular immunity in a host that has been exposed to a particular immunogenic strain.

In one embodiment, the invention is directed to a method for obtaining an immunogenic strain suitable for generating oocysts for use in a vaccine against Coccidiosis. The method involves at least about three cycles or passages of a species of *Eimeria* through donor poultry specimens to obtain an attenuated strain possessing a suitable immunogen. Thus, the method may be utilized to attenuate the *Eimeria* strain, so that it is made both safe and effective for producing oocysts during vaccine development.

In the first cycle, the method involves inoculating specific pathogen free (SPF) donor poultry specimens, preferably one or more donor chickens, with a quantity of oocysts from a species of *Eimeria*. Preferably, the species is a virulent species of *Eimeria* that produces circulating sporozoites in host poultry, and is more preferably *E. acervulina*. The exposure dosage per unit of poultry, e.g. one bird, is within the range of about $10^6$ to about $10^8$ oocysts, and is preferably about $1 \times 10^7$ oocysts. The oocysts are preferably sporulated prior to inoculation using methods available in the art. The number of donor poultry specimens may vary somewhat, but is usually within the range of about 3 to about 15 chickens, preferably about 3 to about 12 chickens, with young, post-hatch chickens or chicks being preferred.

Next, at least some of the donor chicks are bled, preferably at about 3 hours to about 6 hours post-inoculation (p.i.), more preferably at about 3 hours p.i. Blood collected from these donor chicks is then used to inoculate, preferably orally into the crop, another group of SPF poultry specimens. Oocysts are then collected from this group of birds which have been inoculated with the blood samples. These oocysts are preferably collected from the feces of the infected birds. These collected oocysts are then multiplicated on a further set of SPF poultry specimens. (Multiplication, as the term is used in the art, increases the quantity and/or concentration of oocysts available.) Next, feces are gathered from these infected specimens and oocysts are isolated from the feces. This procedure would complete the first passage or cycle. These oocysts, in turn, are then preferably used for further passages of the parasite in a subsequent cycle.

A passage or cycle would thus comprise the following sub-procedures:
 1) Inoculation of blood donor birds with sporulated oocysts;
 2) Collection of blood samples from the donor birds;
 3) Inoculation of fresh birds with blood obtained from the donor birds;
 4) Collection of oocysts from the birds inoculated with blood samples;
 5) Multiplication of oocysts, and collection thereof, for use in further passages or cycles.

In the second cycle, oocysts found in the feces after multiplication and collection from the first cycle above are then used to inoculate a further set of SPF poultry specimens. The oocysts are desirably sporulated. In a preferred embodiment, the dosage level is higher than for the first cycle above. It is therefore desirable that about $1 \times 10^7$ to about $3 \times 10^7$ of the oocysts obtained from the first cycle be used to initially inoculate the blood donor birds in the second cycle. Preferably, about $2 \times 10^7$ oocysts per dose are utilized or approximately twice the number of oocysts per dose utilized in the first cycle. After this, sub-procedures 2) through 5) described above are repeated on SPF poultry specimens in the second cycle.

In the third cycle, oocysts gathered from the feces of specimens from infected poultry following the second cycle are used to inoculate at least a third set of SPF poultry, for a total of three (3×) passages for the particular strain of *Eimeria*. At the start of the third cycle, it is desirable that about $1 \times 10^7$ to about $3 \times 10^7$ of the oocysts obtained from the second cycle be used to initially inoculate the blood donor birds in the third cycle. Preferably, about $2 \times 10^7$ oocysts per dose are utilized or approximately twice the number of oocysts per dose than was utilized in the first cycle. After this, sub-procedures 2) through 5) described above are again repeated as part of the third cycle.

Those skilled in the art may contemplate additional cycles or passages of the *Eimeria* strain oocysts through additional sets of SPF poultry, but this is less preferred herein for reasons of both cost and time. Applicants have discovered that it is preferred to utilize a total of about three passages or cycles as described above.

A final strain of the *E. acervulina* is then isolated after the above procedure of three cycles, which preferably has been attenuated as a result thereof. The strain is obtained from one or more members of inoculated birds at the completion of the third cycle. The strain is obtained using isolation procedures available in the art. This strain may then be used as an antigen. The strain is inoculated into a further set of SPF poultry to generate oocysts for a vaccine. The oocysts are preferably obtained by harvesting them from the feces of the poultry exposed to the strain. They may also be harvested from the blood, if desired.

A preferred strain of *E. acervulina* has now been isolated and identified as the A3C2A2 strain. It was deposited with the European Collection of Cell Cultures in Wiltshire SP4 0JG, United Kingdom, on Dec. 19, 2001 under provisional accession number 02010911 (and is available therefrom), and will function as a suitable antigenic strain. In general, it has now been found that oocysts generated from a strain of *Eimeria* that has been obtained according to the methodology herein described produce high degrees of immunogenicity when incorporated into a vaccine. It has further been found that these oocysts are also much less pathogenic than those generated from the original (pre-inoculation cycling) strain of *Eimeria*. The oocysts generated according to the process herein described are also typically more highly cross-protective, meaning that they offer protection against a wider range of *Eimeria* species. Thus, a vaccine of the invention using oocysts from *Eimeria*, preferably *E. acervulina*, should desirably offer protection against at least three, and preferably at least four other *Eimeria* species, including without limitation, *E. maxima*, *E. tenella*, *E. necatrix* and *E. brunetti*.

The invention is therefore also intended to cover other antigenic strains, as well as products derived therefrom, e.g. oocysts and vaccines containing such oocysts, having the characteristics of the strain of *E. acervulina* and the concomitant products obtained according to the methodology herein described.

The final vaccine of the invention should contain at least about $10^4$ oocysts, preferably sporulated oocysts, per dose in order to induce a sufficient immunogenic response in an animal. The vaccine may also contain a higher quantity of oocysts per dose, such as at least about $10^5$ oocysts per dose, and a range of about $10^4$ to about $10^6$ oocysts per dose is therefore desirable. By the term "sufficient immunogenic response" it is meant a response that will be generally recognized in the art as indicating that a certain level of immunity against Coccidiosis has been conferred such that a significant portion of vaccinated birds are protected against death, disease or depressed performance as a result of a challenge with virulent *Eimeria*.

The vaccine herein described may be administered orally, subcutaneously, intradermally, intramuscularly, intraperitoneally, intravenously or intranasally, as well as other routes of administration known in the art. Of the foregoing, an oral route of administration is generally preferred. Thus, the vaccine may be administered to young poultry via their drinking water, or through mass feeding, for example. The vaccine may be given in ovo, but is generally given to young animals post ovum, with those that are a few hours to a few weeks old generally being the best candidates. Generally, one dose per animal is contemplated, but follow-up boosters are also within the scope of the invention.

The vaccine of the invention is formulated with a pharmaceutically acceptable carrier that can include aqueous media, as well as suspensions or emulsions and the like. The carrier can also include salts, preservatives, pH buffers, stabilizers, and emulsifiers available in the art. In addition, the vaccine may also contain one or more adjuvants to improve performance or increase activity, such as the immune response, and can therefore include materials such as oils, muramyl dipeptide, aluminum hydroxide, saponin, polyanions, amphipatic substances and the like. A preferred quantity of pharmaceutically acceptable carrier per dose (including any adjuvant(s)) is therefore within the range of about 0.001 to about 10 mL, with about 0.1 to about 5 mL being preferred, and about 0.5 to about 1 mL being even more desirable.

The vaccine herein described may also contain other immunogenic agents of poultry. Thus, immunogens related to the pathogens responsible for such diseases as Newcastle Disease Virus (NDV), for example, may also be formulated as part of the vaccine of the invention. Thus, the vaccine herein described may be monovalent, or may also be di-, tri-, tetra- or pentavalent, etc.

The following examples are provided to illustrate various preferred aspects of the invention, but should not be construed as limiting the scope thereof.

EXAMPLES

The following examples are provided by way of illustration only, and should not be construed as limiting the scope of the invention.

1. Materials and Methods 1.1 Materials 1.1.1 Chicks and Husbandry

Male Arbor Acres broilers free from coccidiosis obtained from the commercial Arbor Acres hatchery, Putten, The Netherlands, were housed in cages under isolated conditions at one day of age. Part of the chicks were used as donor chicks and these donor chicks were inoculated with sporulated *E. acervulina* oocysts at 14 days of age. All donor birds for one passage were housed in one cage.

Donor chicks were bled, three at a time, at 3 or 6 hours post-inoculation (p.i.) and each separate blood sample was used to inoculate three other chicks. Birds that received blood from one donor chick were housed in one cage. Feces were examined for oocysts and oocysts from selected positive samples were used for the next passage. Three serial passages were made to obtain the final antigenic strain.

Oocysts from selected positive samples were multiplicated on four SPF chicks per sample before the next passage. SPF chicks were obtained from the Animal Health Service, Deventer, The Netherlands, and were group-housed in isolators.

The pathogenicity of harvested oocysts after passage 1 and 3 was determined and compared to the pathogenicity of the original strain using 10 male Arbor Acres broilers free from coccidiosis per dose and four doses per strain, 80 birds per passage in total. Part of the chicks used for determination of the pathogenicity of oocysts harvested after passage 3 was also used to determine the immunogenicity of these oocysts after re-inoculation with the original strain in comparison to the immunogenicity of the original strain. The chicks were group-housed in cages under isolated conditions.

All birds were housed in the animal facilities of the Animal Health Service, Deventer, The Netherlands, in house 3 of Het Spelderholt located at Beekbergen, The Netherlands, and were fed with food without anti-coccidial additives.

First passage

For the first passage, 26 broilers were used. Eight donor chicks were inoculated with sporulated *E. acervulina* oocysts and six donor chicks were bled, three at a time, at 3 and 6 hours p.i. Each of the six separate blood samples was used to inoculate three other chicks and oocysts purified from two positive feces samples were multiplicated on SPF chicks. The pathogenicity of one multiplicated isolate was determined. Groups and number of chicks are shown below.

| group | no. chicks | use |
|---|---|---|
| D | 8 | donor chick |
| A1, A2, A3 | 3 × 3 | chicks inoculated with blood taken 3 hours p.i. |
| B1, B2, B3 | 3 × 3 | chicks inoculated with blood taken 6 hours p.i. |
| I1, I2 | 2 × 4 | multiplication of oocysts of two positive samples (A2 and A3) |
| pathogenicity | 2 × 40 | pathogenicity of first passage and original strain |

Next passages

For each of the next two passages, 15 broilers were used. Six donor chicks were inoculated with sporulated *E. acervulina* oocysts and three donor chicks were bled at 3 hours p.i. Each separate blood sample was used to inoculate three other chicks and oocysts purified from all positive feces samples were multiplicated on SPF chicks. The pathogenicity and immunogenicity of the multiplicated isolate after passage 3 was determined. Groups and number of chicks are shown below.

| group | no. chicks | use |
|---|---|---|
| D | 6 | donor chick |
| A, B, C | 3 × 3 | chicks inoculated with blood taken 3 hours p.i. |
| I | 2 × 4 | multiplication (2×) of oocysts from positive samples |
| pathogenicity | 2 × 40 | pathogenicity/immunogenicity of passage 3 and original strain |

1.1.2 Inocula

*E. acervulina* was originally obtained from the Central Veterinary Laboratory, Weybridge, UK, and was passaged at the Animal Health Service, Deventer, The Netherlands. For the first passage of extra-intestinal sporozoites, a suspension in saline containing $10^7$ sporulated *E. acervulina* oocysts per ml was prepared. For the next two passages, suspensions in saline containing $2\times10^7$ sporulated *E. acervulina* oocysts per ml obtained after multiplication of the previous passage were prepared.

1.2 Methods 1.2.1 Inoculations

Donor chicks were inoculated orally into the crop with $10^7$ ($1^{st}$ passage) or $2\times10^7$ (next passages) sporulated *E. acervulina* oocysts in 1 ml saline per chick at 14 days of age. The chicks were deprived from food during 12 hours before inoculation. Part of the donor chicks were bled by heart punction, three at a time, at 3 or 6 hours p.i. Blood was collected in 10 ml heparinized tubes, containing 15 IE lithium-heparine per ml blood (Sarstedt, Etten-Leur). The chicks were anaesthetized by intramuscular injection of xylazine (Rompun, 5 mg/kg body weight) and ketamine (25 mg/kg body weight), obtained from AUV, Cuijck, The Netherlands.

Each separate blood sample was used to inoculate three other chicks orally into the crop with 3 ml heparinized blood per chick at 14 days of age. Ten minutes before inoculation, the birds received orally 1 ml of an alkaline suspension composed of 10 Rennie tablets obtained from a commercial druggist's shop, containing 680 mg calcium carbonate and 80 mg magnesium carbonate per tablet, suspended in 20 ml tap water.

1.2.2 Isolation of Oocysts

Feces from remaining donor birds and birds inoculated with blood were collected per cage and per 24 hours at days 3 through 6 or 7 p.i. and oocysts were counted as described below. Oocysts were purified from collected feces if oocyst counts were positive using a salt flotation technique. After purification, the isolated oocysts were suspended in a 2% (w/v) solution of potassium bichromate and the suspensions were aerated by air bubbles using common aquarium techniques for 48 hours at 29° C. to induce sporulation of the oocysts. Thereafter, oocysts in the suspensions were counted.

Sporulated oocysts were multiplicated on four SPF birds per sample. At six days of age, SPF birds were inoculated orally into the crop with 3 ml sporulated oocysts obtained from feces samples. Feces from SPF birds was collected per cage at days 4 through 6 p.i. and oocysts were purified from the feces and counted.

For multiplication after passage 1, birds in groups I1 and I2 received oocysts isolated from feces samples A2 and A3, containing 10,000 and 45,000 oocysts in total, respectively. Isolates obtained after the next passages were multiplicated twice because of the low number of oocysts in the isolates.

1.2.3 Counting Oocysts in Feces

About 25 fresh droppings were collected per cage and a maximum of 100 g feces was weighed, suspended in a 10% (w/v) solution of sodium chloride (density=1.1) and mixed until homogeneous. Aliquots of 1 ml of suspended feces were mixed in 9 ml of a saturated solution of sodium chloride. Oocysts were counted in triplicate samples of the diluted suspended feces using a counting chamber according to Hawkley and the number of oocysts per gram feces was calculated.

1.2.4 Pathogenicity

The pathogenicity of oocysts after passage 1 and 3 was determined and compared to the pathogenicity of the original strain using 10 broilers per dose and four doses per sample. Dosages of $10^3$, $10^4$, $10^5$ and $10^6$ sporulated oocysts per bird were inoculated orally at 8 days of age. The chicks were group-housed in cages. Feces was collected per cage at days 4 through 6 or 7 p.i. and oocysts in the feces were counted as described above. At 6 days p.i., birds were euthanized by electrocution. All euthanized birds were autopsied and lesions of the intestines were scored according to Johnson and Reid (1).

For determination of the pathogenicity of oocysts harvested after passage 1, all birds were euthanized at 6 days p.i. and weighed. For determination of the pathogenicity of oocysts harvested after passage 3, five birds of each group were euthanized at 6 days p.i. and the remaining birds were used to determine the immunogenicity. Feces was collected per cage from 10 birds per cage at days 4 through 6 and from 5 birds per cage on day 7 p.i.

1.2.5 Immunogenicity

The immunogenicity of harvested oocysts after passage 3 was determined and compared to the immunogenicity of the original strain using five broilers of each group used for the determination of pathogenicity. All birds were weighed and re-inoculated orally with $10^5$ sporulated oocysts of the original strain per bird at 9 days p.i. Feces was collected per cage at days 4 through 6 p.i. and oocysts in the feces were counted as described above. At 6 days after re-inoculation, all birds were euthanized by electrocution and weighed. All birds were autopsied and lesions of the intestines were scored as described above.

2. Results 2.1 Isolation of Oocysts

First passage

No oocysts were found in the feces of inoculated chicks at 3 days p.i. Oocysts were found in the feces of birds inoculated with blood obtained from donor birds at 3 hours p.i. rather than in the feces of birds inoculated with blood obtained at 6 hours p.i. All feces samples of groups A2 and A3 were positive for oocysts at 5 days p.i. and oocysts were purified from feces of these groups. After sporulation, the following samples were obtained:

| group | oocysts/ml | total volume (ml) |
|-------|------------|-------------------|
| A2    | 3,000      | 25                |
| A3    | 15,000     | 25                |

Oocysts harvested from groups A2 and A3 were multiplicated in SPF birds. After multiplication, oocysts in the feces of birds that received oocysts isolated from group A2 had shrunken and viability of these oocysts was not clear. From birds of group I2 that received oocysts isolated from group A3, 500 ml containing 290,000.oocysts per ml was harvested and the pathogenicity of these oocysts was determined.

Second passage

One feces sample of group C was positive for oocysts at 5 and 6 days p.i. and oocysts were purified from feces collected on these days. The isolate called A3C2 contained a low number of oocysts and oocysts were multiplicated in SPF birds. After multiplication, $24 \times 10^6$ oocysts were harvested and these oocysts were multiplicated once again in SPF birds.

Third passage

One feces sample of group A was positive for oocysts at 5 days p.i. and oocysts were purified from the feces. The isolate called A3C2A2 contained a low number of oocysts and oocysts were multiplicated twice in SPF birds. After multiplication, oocysts were harvested and pathogenicity and immunogenicity of these oocysts was determined 2.2 Pathogenicity The pathogenicity of oocysts harvested after passages 1 and 3 was determined. The results are summarized in Tables 1 and 2. After passage 1, no clear differences in mean body weight, mean lesion score or number of oocysts per gram feces were observed.

TABLE 1

Pathogenicity after first passage.

pathogenicity of strains of *E. acervulina*

| dose: | | isolate A3 | | | Original strain | |
|---|---|---|---|---|---|---|
| (oocysts per bird) n = 10 | mean body weight (g) | mean lesion score | no. oocysts per g feces $(\times 10^3)$* | mean body weight (g) | Mean lesion score | no. oocysts per g feces $(\times 10^3)$* |
| $10^3$ | 428 | 1.0 | 480 | 425 | 0.9 | 150 |
| $10^4$ | 414 | 2.1 | 1400 | 426 | 2.2 | 1500 |
| $10^5$ | 391 | 2.9 | 2100 | 378 | 2.5 | 1300 |
| $10^6$ | 332 | 3.1 | 528 | 350 | 3.1 | 920 |

*collected days 4 through 6.

After passage 3, mean lesion scores were lower with oocysts of passage 3 than with oocysts of the original strain after dosages of $10^4$ oocysts or more per bird. However, no clear differences in number of oocysts per gram feces were observed compared to the original strain. The number of oocysts was according to the inoculated dose in both cases. The number of oocysts in the feces of birds that received the higher dosages of the isolated strain indicates that these birds were severely infected but that the lesion score did not increase with the inoculated dose.

TABLE 2

Pathogenicity after third passage.

pathogenicity of strains of *E. acervulina*

| dose: (oocysts per bird) n = 5 | mean body weight (g) | mean lesion score | no. oocysts per g feces $(\times 10^3)$* | mean body weight (g) | Mean lesion score | no. oocysts per g feces $(\times 10^3)$* |
|---|---|---|---|---|---|---|
| $10^3$ | not done | 1.0 | 270 | not done | 1.2 | 110 |
| $10^4$ | not done | 1.6 | 710 | not done | 2.6 | 1800 |
| $10^5$ | not done | 1.0 | 510 | not done | 3.2 | 650 |
| $10^6$ | not done | 1.2 | 960 | not done | 3.5 | 910 |

*collected days 4 through 7.

2.3 Immunogenicity

The immunogenicity of oocysts harvested after passage 3 was determined. The results are summarized in Table 3. In the group inoculated with $10^3$ oocysts per bird few lesions were observed. Also oocysts were found in the feces of this group. In groups inoculated with the higher dosages of the isolated strain, no lesions and no oocysts in the feces were observed. All groups inoculated with dosages of $10^4$ oocysts per bird of the isolated strain or above were protected against re-inoculation with the original strain. These results should be compared with the control group (right-hand side) that were re-inoculated with the original strain after surviving exposure from the original strain.

TABLE 3

Immunogenicity after third passage.

| dose: | isolate A3C2A2 | | | Original strain | | |
|---|---|---|---|---|---|---|
| (oocysts per bird) n = 5 | mean growth (g)* | mean lesion score | no. oocysts per g feces (×10³)** | mean growth (g)* | Mean lesion score | no. oocysts per g feces (×10³)** |
| 10³ | 356 | 0.25 | 260 | 304 | 0 | 169 |
| 10⁴ | 323 | 0 | 0 | 314 | 0 | 0 |
| 10⁵ | 335 | 0 | 0 | 342 | 0 | 0 |
| 10⁶ | 304 | 0 | 0 | 325 | 0 | 1 |

*after re-inoculation; **collected days 4 through 6.

3. Discussion of Results

After multiplication, oocysts in the feces of birds that received oocysts isolated after the first passage from group A2 had shrunken and viability of these oocysts was not clear. This may be due to the time that these oocysts had been exposed to the saturated salt solution during purification. No deviations of the oocysts were observed before multiplication.

The first passage of extra-intestinal oocysts of *E. acervulina* succeeded with group A3 but reproducibility and pathogenicity of the isolated oocysts was not different from the original *E. acervulina* strain.

The number of oocysts in the feces of birds that received the higher dosages of passage 3 of the isolated strain indicated that these birds were severely infected. However, the lesion score did not increase with the inoculated dose. If the lesion score is a good parameter for pathogenicity of the strain, then the isolated strain A3C2A2 is considerably less pathogenic than the original strain of *E. acervulina*.

After re-inoculation with the original strain, birds inoculated with $10^3$ oocysts of the isolated strain A3C2A2 per bird showed few lesions and oocysts were found in the feces of this group. Birds inoculated with dosages of $10^4$ oocysts per bird of the isolated strain A3C2A2 or above were protected against re-inoculation with the original strain.

The following tables A1 through A6 further quantify the results of the experiments heretofore performed.

4. References

1. Johnson J K, Reid W M. "Anticoccidial drugs: Lesion scoring techniques in battery and floor pen experiments with chickens" Exp. Parasitol. 1970; 28: 30–36.

TABLE A1

Oocyst in feces of donor birds and birds inoculated with blood after passage 1.

no. oocysts per counting chamber in feces of indicated day p.i.

| group | day 3 | | | day 4 | | | day 5 | | | day 6 | | |
|---|---|---|---|---|---|---|---|---|---|---|---|---|
| D | 40 | 40 | 40 | 330 | 330 | 330 | 250 | 250 | 250 | 50 | 50 | 50 |
| A1 | neg. | neg. | neg. | 5 | 5 | 5 | neg. | neg. | Pos. | neg. | neg. | pos. |
| A2 | neg. | neg. | neg. | pos. | pos. | pos. | pos. | pos. | Pos. | neg. | neg. | pos. |
| A3 | neg. | neg. | neg. | pos. | pos. | pos. | pos. | pos. | Pos. | pos. | pos. | pos. |
| B1 | neg. | neg. | neg. | neg. | 1 | 1 | neg. | neg. | Neg. | neg. | neg. | neg. |
| B2 | neg. | neg. | neg. | pos. | pos. | pos. | neg. | neg. | Pos. | neg. | neg. | neg. |
| B3 | neg. | neg. | neg. | neg. | neg. | neg. | neg. | neg. | Neg. | neg. | neg. | neg. |

TABLE A2

Oocyst in feces of donor birds and birds inoculated with blood after passage 2.

no. oocysts per counting chamber in feces of indicated day p.i.

| group | day 3 | | | day 4 | | | day 5 | | | day 6 | | | day 7 | | |
|---|---|---|---|---|---|---|---|---|---|---|---|---|---|---|---|
| D | neg. | pos. | pos. | pos. | pos. | pos. | pos. | pos. | pos. | Pos. | pos. | pos. | pos. | pos. | pos. |
| A | neg. | neg. | neg. | neg. | neg. | neg. | neg. | neg. | pos. | Neg. | neg. | neg. | neg. | neg. | neg. |
| B | neg. | neg. | neg. | neg. | neg. | neg. | neg. | neg. | neg. | Neg. | neg. | neg. | neg. | neg. | neg. |
| C | neg. | neg. | neg. | neg. | neg. | neg. | neg. | neg. | pos. | Neg. | neg. | pos. | neg. | neg. | neg. |

TABLE A3

Oocyst in feces of donor birds and birds inoculated with blood after passage 3.

no. oocysts per counting chamber in feces of indicated day p.i.

| group | day 3 | | day 4 | | | day 5 | | | Day 6 | | | day 7 | | |
|---|---|---|---|---|---|---|---|---|---|---|---|---|---|---|---|
| D | not done | pos. | pos. | pos. | pos. | pos. | pos. | pos. | Pos. | Pos. | pos. | pos. | pos. | pos. | pos. |
| A | not done | neg. | neg. | neg. | neg. | neg. | neg. | pos. | Neg. | Neg. | neg. | neg. | neg. | neg. | neg. |

TABLE A3-continued

Oocyst in feces of donor birds and birds inoculated with blood after passage 3.

no. oocysts per counting chamber in feces of indicated day p.i.

| group | day 3 | | day 4 | | | day 5 | | | Day 6 | | day 7 | |
|---|---|---|---|---|---|---|---|---|---|---|---|---|
| B | not done | neg. | neg. | pos. | neg. | neg. | neg. | Neg. | Neg. | neg. | neg. | neg. | neg. |
| C | not done | neg. | neg. | neg. | neg. | neg. | neg. | Neg. | Neg. | neg. | neg. | neg. | neg. |

TABLE A4

Individual results on determination of pathogenicity after the first passage.

pathogenicity of strains of *E. acervulina*

| | isolated from group A3 | | Original strain | |
|---|---|---|---|---|
| Group/bird | body weight (g) | lesion score | body weight (g) | lesion score |
| $10^3$ | | | | |
| 1 | 429 | 1 | 432 | 1 |
| 2 | 413 | 1 | 417 | 1 |
| 3 | 424 | 1 | 416 | 1 |
| 4 | 424 | 1 | 411 | 1 |
| 5 | 450 | 1 | 463 | 1 |
| 6 | 441 | 1 | 451 | 0 |
| 7 | 393 | 1 | 385 | 1 |
| 8 | 432 | 1 | 416 | 1 |
| 9 | 422 | 1 | 457 | 1 |
| 10 | 450 | 1 | 406 | 1 |
| $10^4$ | | | | |
| 1 | 426 | 2 | 424 | 1 |
| 2 | 448 | 2 | 453 | 2 |
| 3 | 442 | 2 | 441 | 2 |
| 4 | 428 | 2 | 413 | 2 |
| 5 | 456 | 3 | 434 | 3 |
| 6 | 395 | 3 | 437 | 1 |
| 7 | 364 | 2 | 407 | 2 |
| 8 | 360 | 1 | 436 | 3 |
| 9 | 409 | 2 | 356 | 3 |
| 10 | 408 | 2 | 461 | 3 |
| $10^5$ | | | | |
| 1 | 393 | 2 | 397 | 2 |
| 2 | 388 | 3 | 378 | 2 |
| 3 | 389 | 3 | 432 | 2 |
| 4 | 419 | 3 | 393 | 3 |
| 5 | 410 | 2 | 390 | 2 |
| 6 | 328 | 3 | 333 | 3 |
| 7 | 438 | 3 | 379 | 3 |
| 8 | 354 | 3 | 308 | 3 |
| 9 | 439 | 4 | 392 | 3 |
| 10 | 352 | 3 | 378 | 2 |
| $10^6$ | | | | |
| 1 | 333 | 3 | 420 | 3 |
| 2 | 348 | 2 | 345 | 3 |
| 3 | 323 | 3 | 338 | 3 |
| 4 | 351 | 3 | 336 | 3 |
| 5 | 355 | 4 | 394 | 3 |
| 6 | 282 | 3 | 312 | 3 |
| 7 | 354 | 4 | 271 | 4 |
| 8 | 346 | 3 | 412 | 3 |
| 9 | 293 | 3 | 349 | 3 |
| 10 | 332 | 3 | 326 | 3 |

TABLE A5

Individual results on determination of pathogenicity after the third passage.

pathogenicity of strains of *E. acervulina*

| | isolate A3C2A2 | | Original strain | |
|---|---|---|---|---|
| group/bird | body weight (g) | lesion score | body weight (g) | lesion score |
| $10^3$ | | | | |
| 1 | notdone | 1.00 | not done | 1.00 |
| 2 | | 1.00 | | 1.00 |
| 3 | | 1.00 | | 2.00 |
| 4 | | 1.00 | | 1.00 |
| 5 | | 1.00 | | 1.00 |
| $10^4$ | | | | |
| 1 | notdone | 2.00 | not done | 4.00 |
| 2 | | 2.00 | | 3.00 |
| 3 | | 1.00 | | 2.00 |
| 4 | | 2.00 | | 2.00 |
| 5 | | 1.00 | | 2.00 |
| $10^5$ | | | | |
| 1 | notdone | 1.00 | not done | 4.00 |
| 2 | | 1.00 | | 3.00 |
| 3 | | 1.00 | | 4.00 |
| 4 | | 1.00 | | 3.00 |
| 5 | | 1.00 | | 2.00 |
| $10^6$ | | | | |
| 1 | notdone | 1.00 | not done | 4.00 |
| 2 | | 1.00 | | 4.00 |
| 3 | | 1.00 | | 3.00 |
| 4 | | 2.00 | | 3.00 |
| 5 | | 1.00 | | not done |

TABLE A6

Individual results on determination of immunogenicity after the third passage.

immunogenicity of strains of *E. acervulina*

| | isolate A3C2A2 | | | Original strain | | |
|---|---|---|---|---|---|---|
| | body weight (g) | | | Body weight (g) | | |
| Group/bird | before reinoculation | 6 days post reinoculation | lesion score | before reinoculation | 6 days post reinoculation | lesion score |
| $10^3$ | | | | | | |
| 1 | 594 | 912 | 0.00 | 644 | 953 | 0.00 |
| 2 | 620 | 1030 | 0.00 | 547 | 832 | 0.00 |
| 3 | 674 | 991 | 1.00 | 592 | 847 | 0.00 |
| 4 | 653 | 1031 | 0.00 | 635 | 970 | 0.00 |

TABLE A6-continued

Individual results on determination of immunogenicity after the third passage.

| | immunogenicity of strains of *E. acervulina* | | | | | |
|---|---|---|---|---|---|---|
| | isolate A3C2A2 | | | Original strain | | |
| | body weight (g) | | | Body weight (g) | | |
| Group/bird | before reinoculation | 6 days post reinoculation | lesion score | before reinoculation | 6 days post reinoculation | lesion score |
| 5 | not done | not done | not done | 533 | 870 | 0.00 |
| $10^4$ | | | | | | |
| 1 | 503 | 839 | 0.00 | 555 | 871 | 0.00 |
| 2 | 609 | 953 | 0.00 | 610 | 969 | 0.00 |
| 3 | 551 | 859 | 0.00 | 579 | 852 | 0.00 |
| 4 | 513 | 798 | 0.00 | 624 | 942 | 0.00 |
| 5 | 550 | 890 | 0.00 | 480 | 782 | 0.00 |
| $10^5$ | | | | | | |
| 1 | 588 | 1013 | 0.00 | 580 | 951 | 0.00 |
| 2 | 548 | 919 | 0.00 | 584 | 953 | 0.00 |
| 3 | 420 | 696 | 0.00 | 557 | 903 | 0.00 |
| 4 | 403 | 670 | 0.00 | 539 | 884 | 0.00 |
| 5 | 560 | 897 | 0.00 | 498 | 778 | 0.00 |
| $10^6$ | | | | | | |
| 1 | 482 | 791 | 0.00 | 568 | 928 | 0.00 |
| 2 | 470 | 789 | 0.00 | 512 | 856 | 0.00 |
| 3 | 495 | 819 | 0.00 | 552 | 858 | 0.00 |
| 4 | 498 | 719 | 0.00 | 440 | 709 | 0.00 |
| 5 | 471 | 818 | 0.00 | 485 | 803 | 0.00 |

While the invention has been described in each of its various embodiments, it is within the scope thereof that certain modifications may be undertaken by the person skilled in the art without departing from the invention's true spirit and scope.

What is claimed is:

1. A method for obtaining an immunogenic strain useful for producing a vaccine against Coccidiosis, which comprises the cycle of: a) infecting at least one first specific pathogen-free donor bird with oocysts of an *Eimeria* species; b) collecting sporozoite- containing blood from said donor bird at about 3 to about 6 hours post-inoculation; c) infecting at least one second specific pathogen-free bird with said blood; d) collecting oocysts from said second bird; and e) multiplicating said oocysts; and then repeating said cycle using said multiplicated oocysts from part e), wherein about three cycles of said method are completed.

2. The method of claim 1, wherein the oocysts collected in step (d) are collected from the feces of said second bird.

3. The method of claim 1, further comprising isolating said immunogenic strain.

4. The method of claim 3, further comprising generating oocysts from said immunogenic strain.

5. The method of claim 4, further comprising formulating a vaccine from said generated oocysts.

6. The method of claim 5, wherein said vaccine is formulated using about $10^4$ oocysts.

7. The method of claim 1, wherein said repeating comprises infecting said poultry with about twice the number of oocysts per dose than was utilized in the first cycle.

8. The method of claim 1, which comprises carrying out a total of three cycles.

9. The method of claim 1, wherein said infecting of said first donor bird comprises administering about $1\times10^6$ to about $3\times10^8$ of said oocysts.

10. The method of claim 9, wherein said infecting comprises administering about $1\times10^7$ oocysts.

11. The method of claim 10, wherein said repeating comprises administering about $2\times10^7$ oocysts in part a).

12. The method of claim 5, which comprises formulating said vaccine using about $10^5$ oocysts.

13. The method of claim 1, further comprising sporulating said oocysts prior to administration to said bird.

14. The method of claim 1, wherein said *Eimeria* species is *E. acervulina*.

15. The method of claim 1, wherein the donor bird is a chick.

* * * * *

UNITED STATES PATENT AND TRADEMARK OFFICE
CERTIFICATE OF CORRECTION

PATENT NO. : 6,998,126 B2
APPLICATION NO. : 10/371914
DATED : February 14, 2006
INVENTOR(S) : Frans G. Davelaar It is certified that error appears in the above-identified patent and that said Letters Patent is hereby corrected as shown below:

In column 10, Line 40 Table 2 should read

-- Table 2.
Pathogenicity after third passage.

| dose: (oocysts per bird) n=5 | pathogenicity of strains of E. acervulina | | | | | |
|---|---|---|---|---|---|---|
| | isolate A3C2A2 | | | Original Strain | | |
| | mean body weight (g) | mean lesion score | no. oocysts per g feces (x10³)* | mean body weight (g) | Mean lesion score | no. oocysts per g feces (x10³)* |
| 10³ | not done | 1.0 | 270 | not done | 1.2 | 110 |
| 10⁴ | not done | 1.6 | 710 | not done | 2.6 | 1800 |
| 10⁵ | not done | 1.0 | 510 | not done | 3.2 | 650 |
| 10⁶ | not done | 1.2 | 960 | not done | 3.5 | 910 |

* collected days 4 through 7. --.

Signed and Sealed this

Tenth Day of June, 2008

JON W. DUDAS
*Director of the United States Patent and Trademark Office*